United States Patent [19]
Yanagi et al.

[11] Patent Number: 5,767,286
[45] Date of Patent: Jun. 16, 1998

[54] PROCESS FOR THE PREPARATION OF 1-4-DISUBSTITUTED-5 (4H)-TETRAZOLINONES

[75] Inventors: Akihiko Yanagi, Tochigi; Yukiyoshi Watanabe, Saitama; Shin-ichi Narabu, Ibaraki, all of Japan

[73] Assignee: Nihon Bayer Agrochem K. K., Tokyo, Japan

[21] Appl. No.: 311,643

[22] Filed: Sep. 23, 1994

[30] Foreign Application Priority Data

Sep. 30, 1993 [JP] Japan .................. 5-265417

[51] Int. Cl.⁶ .............. C07D 401/06; C07D 401/14; C07D 257/04
[52] U.S. Cl. .............. 548/251; 546/276; 546/208
[58] Field of Search .............. 548/251; 546/210, 546/276

[56] References Cited

U.S. PATENT DOCUMENTS

| | | | |
|---|---|---|---|
| 4,618,365 | 10/1986 | Covey et al. | 71/92 |
| 4,985,065 | 1/1991 | Theodoridis | 71/92 |

FOREIGN PATENT DOCUMENTS

| | | |
|---|---|---|
| 0202929 | 11/1986 | European Pat. Off. . |
| 0571854 | 12/1993 | European Pat. Off. . |
| 0571855 | 12/1993 | European Pat. Off. . |
| 0572855 | 12/1993 | European Pat. Off. . |
| 0578090 | 1/1994 | European Pat. Off. . |
| 0612735 | 8/1994 | European Pat. Off. . |

*Primary Examiner*—David B. Springer
*Attorney, Agent, or Firm*—Sprung Kramer Schaefer & Briscoe

[57] ABSTRACT

1,4-Disubstituted-5(4H)-tetrazolinones of the formula (I)

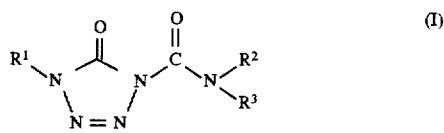

wherein $R^1$, $R^2$ and $R^3$ have the meanings given in the specification), which are known to be useful as herbicides, can be obtained in very good yields by reacting the corresponding 1-substituted-5(4H)-tetrazolinones with the corresponding carbamoyl chlorides in the presence of 4-dimethylaminopyridine.

6 Claims, 5 Drawing Sheets

PROCESS FOR THE PREPARATION OF 1-4-DISUBSTITUTED-5 (4H)-TETRAZOLINONES

The present invention relates to a novel process for the production of known 1,4-disubstituted-5(4H)-tetrazolinones which can be utilized, for example, as agricultural chemicals.

Regarding the synthesis of tetrazolinones of the type of general formula (I) below, U.S. Pat. No. 4,618,365 discloses a process wherein a tetrazolinone of the general formula:

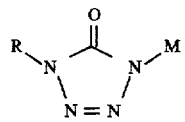

wherein

M represents hydrogen or an alkali metal such as Li, Na or K is reacted with a carbomyl chloride.

Concerning the above-mentioned reaction, when use is made, as M, of a hydrogen atom, it is preferably carried out in the presence of a suitable acid-acceptor such as pyridine, a trialkylamine, or the like. Further, in this reaction, use may be made, as suitable solvents, of acetone, acetonitrile, toluene, chloroform, and the like.

However, such known process produces, in addition to the desired tetrazolinones, the isomeric compounds of the general formula (A):

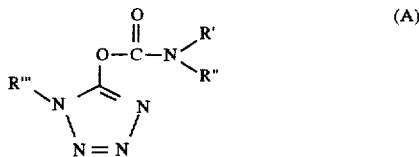

(hereinafter referred to as "O-carbamoyl compounds") as by-products and the production rate of such by-products sometimes turns out to be as much as one third of the production rate of the desired compounds (FIGS. 1 to 5).

The O-carbamoyl compound by-products do not exhibit herbicidal activity as comparable to the desired N-carbamoyl tetrazolinones. Further, such O-carbamoyl compounds are chemically unstable, i.e. they are readily hydrolyzable by aqueous acids and alkali so that the separation and removal of O-carbamoyl compounds from the desired N-carbamoyl products (I) is difficult.

Thus the known process has serious inherent defects, viz. with regard to reaction procedure and reaction efficiency.

To solve the above-mentioned technical problem, there has now been found a process—with two process variants (a) and (b)—for selectively producing 1,4-disubstituted-5 (4H)-tetrazolinones of the general formula (I),

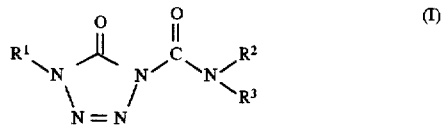

wherein $R^1$ represents optionally substituted $C_{1-12}$ alkyl, optionally substituted $C_{3-8}$ cycloalkyl, optionally substituted $C_{3-8}$ alkenyl, optionally substituted $C_{3-8}$ alkynyl, or a group of the general formula

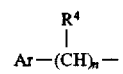

wherein

Ar represents optionally substituted phenyl, optionally substituted naphthyl or an optionally substituted five- to seven-membered heterocyclic ring, $R^4$ represents hydrogen or $C_{1-4}$ alkyl, and n is 0, 1, 2, 3 or 4, $R^2$ and $R^3$ each represents, independently, $C_{1-8}$ alkyl, $C_{1-6}$ haloalkyl, $C_{2-6}$ alkoxyalkyl, $C_{2-6}$ alkylthioalkyl, $C_{2-6}$ alkenyl, $C_{2-6}$ haloalkenyl, $C_{3-6}$ alkynyl, $C_{1-4}$ alkoxy, $C_{1-4}$ haloalkoxy, $C_{3-8}$ cycloalkyl, optionally substituted phenyl or optionally substituted aralkyl, or $R^2$ and $R^3$ together with the adjacent N atom may form a ring, which process comprises (a) reacting a compound of the general formula (II),

wherein $R^1$ has the same meaning as mentioned above, with a compound of the general formula (III)

wherein $R^2$ and $R^3$ have the same meaning as mentioned above, in the presence of 4-dimethylamino-pyridine and optionally in the presence of a diluent and of an additional acid-binder, or (b) reacting a compound of the above-mentioned general formula (II) with a compound of the above-mentioned general formula (III), optionally in the presence of a diluent and of an acid-binder other than 4-dimethylamino-pyridine, to obtain a mixture consisting of a tetrazolinone of the above-mentioned general formula (I) and a compound of the general formula (IV),

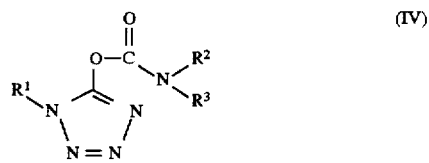

wherein $R^1$, $R^2$ and $R^3$ have the same meanings as mentioned above, (first step), followed by reacting said obtained mixture with 4-dimethyl-amino-pyridine, optionally in the presence of a diluent, thereby effecting conversion of the compound(s) of formula (IV) to the desired isomeric compound(s) of the formula (I) by a "carbamoyl-migration" (i.e. 1,3-shift of the carbamoyl group, from O to N) (second step).

The process according to the present invention has surprisingly been found to be able selectively to prepare the desired tetrazolinones of general formula (I) in high yield, either by reacting a compound of general formula (II) with a compound of general formula (III) in the presence of 4-dimethylamino-pyridine (that has not been employed in the prior art processes), or by reacting the above-mentioned starting materials (II) and (III) according to a conventional procedure, followed by reacting the resulting mixture of isomeric compounds of formulas (I) and (IV) with 4-dimethylamino-pyridine, thereby effecting a 1,3-migration of the carbamoyl substituent.

The 4-dimethylamino-pyridine to be employed in the process according to the present invention can be used as acid-acceptor and catalyst, or as catalyst together with another acid-acceptor, as discussed hereinbelow.

The process according to the present invention can be utilized for the prepartion of the many tetrazolinones of general formula (I) and has been found to be most suitable for their production on an industrial scale.

A preferred group of 1,4-disubstituted-5(4H)-tetrazolinones, to be produced according to the present invention, are those compounds of formula (I), wherein $R^1$ represents $C_{1-12}$ alkyl, $C_{1-6}$ haloalkyl, $C_{2-8}$ alkoxyalkyl, $C_{2-8}$ alkylthioalkyl, $C_{3-8}$ cycloalkyl, $C_{3-8}$ alkenyl, $C_{3-8}$ haloalkenyl, $C_{3-8}$ alkynyl, or a group of the general formula

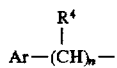

wherein

Ar represents unsubstituted phenyl, or a phenyl group having a substituent or substituents optionally selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxy-carbonyl, carboxy, optionally substituted phenoxy, optionally substituted heterocyclyl-oxy, methylene dioxy, halomethylene dioxy, ethylene dioxy, haloethylene dioxy, cyano, nitro and —$NR^5R^6$; or Ar represents unsubstituted naphthyl, or a substituted naphthyl group having a substituent or substituents optionally selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxy-carbonyl, carboxyl, optionally substituted phenoxy, optionally substituted heterocyclyl-oxy, methylene dioxy, halomethylene dioxy, ethylene dioxy, haloethylene dioxy, cyano, nitro and —$NR^5R^6$; or Ar represents a five- to seven-membered heterocyclic ring or their benzologues or their substituted derivatives having a substituent or substituents optionally selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio $C_{1-4}$ alkoxy-carbonyl, carboxy, optionally substituted phenoxy, optionally substituted heterocyclyl-oxy, methylene dioxy, halomethylene dioxy, ethylene dioxy, haloethylene dioxy, cyano, nitro and —$NR^5R^6$;

$R^4$ represents hydrogen or $C_{1-4}$ alkyl, $R^5$ and R6 may be the same or different and represent hydrogen or $C_{1-4}$ alkyl, and n is 0, 1, 2 or 3; and $R^2$ and $R^3$ each independently represents methyl, ethyl, n-propyl, isopropyl, n-(sec-,iso-, or tert-)butyl, n-pentyl, n-hexyl, trifluoromethyl, difluoromethyl, 2-chloroethyl, 2-fluoroethyl, 2,2,2-trifluoroethyl, 3-fluoropropyl, perfluoropropyl, perfluorohexyl, 2-methoxyethyl, ethoxymethyl, 2-ethoxyethyl, 2-propoxyethyl, 2-methylthioethyl, 3-methylthiopropyl, 2-ethylthioethyl, allyl, 2-(3-, 4-)butenyl, hexenyl, 3-chloroallyl, propargyl, methoxy, ethoxy, n-propoxy, isopropoxy, 3-chloroallyloxy, cyclopropyl, cyclopentyl, cyclohexyl, optionally substituted phenyl or benzyl, (wherein said substituents may be optionally selected from the group consisting of fluorine, chlorine, bromine, methyl, ethyl, n-propyl, isopropyl, tert-butyl, trifluoromethyl, methoxy, ethoxy, isopropoxy, difluoromethoxy, trifluoromethoxy, methylthio, ethoxy, isopropoxy, difluoromethoxy, trifluoromethoxy, methylthio, ethylthio, trifluoromethylthio, 2,2,2-trifluoroethylthio, cyano and nitro), or $R^2$ and $R^3$ together with the adjacent nitrogen atom may form piperidino, 2,6-dimethylpiperidino, morpholino, 2,6-dimethylmorpholino, thiomorpholino, 2,3-dihydroindolyl or perhydroindolyl.

A particularly preferred group of 1,4-disubstituted-5(4H)-tetrazolinones, to be produced according to the present invention, are those compounds of formula (I), wherein $R^1$ represents methyl, ethyl, n-propyl, isopropyl, n-(sec-, iso-, or tert-)butyl, n-hexyl, trifluoromethyl, difluoromethyl, chlorodifluoromethyl, 2,2,2-trifluoroethyl, perfluoropropyl, perfluorohexyl, methoxyethyl, ethoxymethyl, ethoxyethyl, propoxyethyl, butoxyethyl, methylthioethyl, methylthiomethyl, methylthiopropyl, ethylthiomethyl, ethylthioethyl, propylthioethyl, butylthioethyl, cyclopropyl, cyclobutyl, cyclopentyl, cyclohexyl, allyl, chloroallyl, butenyl, hexenyl, propargyl, or a group of the general formula

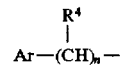

wherein

Ar represents unsubstituted phenyl or a phenyl group having a substituent or substituents optionally selected from the group consisting of fluorine, chlorine, bromine, methyl, ethyl, propyl, butyl, difluoromethyl, chlorodifluoromethyl, trifluoromethyl, 2,2,2-trifluoroethyl, methoxy, ethoxy, propoxy, butoxy, difluoromethoxy, chlorodifluoromethoxy, trifluoromethoxy, 2,2,2-trifluoroethoxy, methylthio, ethylthio, propylthio, difluoromethylthio, trifluoromethylthio, 2,2,2-trifluoroethylthio, dimethylamino, diethylamino, methoxycarbonyl, ethoxycarbonyl, butoxycarbonyl, carboxy, phenoxy, optionally substituted heterocyclyl-oxy, (wherein the hetero ring of said heterocyclyl-oxy is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, benzothiophene, furan and benzofuran), methylenedioxy, difluoromethylenedioxy, ethylenedioxy, chlorodifluoroethylenedioxy, difluoroethylenedioxy, trifluoroethylenedioxy, tetrafluoroethylenedioxy, cyano and nitro; or Ar represents unsubstituted naphthyl or a substituted naphthyl group having a substituent or substituents optionally selected from the group consisting of fluorine, chlorine, bromine, methyl, ethyl, propyl, butyl, difluoromethyl, chlorodifluoromethyl, trifluoromethyl, 2,2,2-trifluoroethyl, methoxy, ethoxy, propoxy, butoxy, difluoromethoxy, chlorodifluoromethoxy, trifluoromethoxy, 2,2,2-trifluoroethoxy, methylthio, ethylthio, propylthio, difluoromethylthio, trifluoromethylthio, 2,2,2-trifluoroethylthio, dimethylamino, diethylamino, methoxycarbonyl, ethoxycarbonyl, butoxycarbonyl, carboxy, phenoxy, optionally substituted heterocyclyloxy, (wherein the hetero ring of said heterocyclyl-oxy is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, benzothiophene, furan and benzofuran), methylenedioxy, difluoromethylenedioxy, ethylenedioxy, chlorodifluoroethylenedioxy, difluoroethylenedioxy, trifluoroethylenedioxy, tetrafluoroethylenedioxy, cyano and nitro; or Ar represents an unsubstituted or substituted five- or six-membered heterocyclic ring and their benzologues, wherein said hetero ring is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, and furan), having a substituent or substituents optionally selected from the group consisting of fluorine, chlorine, bromine, methyl, ethyl, propyl, butyl, difluoromethyl, chlorodifluoromethyl, trifluoromethyl, 2,2,2-trifluoroethyl, methoxy, ethoxy, propoxy, butoxy, difluoromethoxy, chlorodifluoromethoxy, trifluoromethoxy, 2,2,2-trifluoroethoxy, methylthio, ethylthio, propylthio, difluoromethylthio, trifluoromethylthio, 2,2,2-trifluoroethylthio, dimethylamino, diethylamino, methoxycarbonyl, ethoxycarbonyl, butoxycarbonyl, carboxy, phenoxy, optionally substituted heterocyclyloxy, (wherein the hetero ring of said heterocyclyl-oxy is selected from the group consisting of imidazole, pyrazole, triazole, oxazole, isoxazole, benzoxazole, thiazole, isothiazole, benzothiazole, oxadiazole, thiadiazole, tetrazole, pyridine, quinoline, isoquinoline, pyrimidine, pyridazine, pyrazine, quinazoline, quinoxaline, triazine, thiophene, benzothiophene, furan and benzofuran), methylenedioxy, difluoromethylenedioxy, ethylenedioxy, chlorodifluoroethylenedioxy, difluoroethylenedioxy, trifluoroethylenedioxy, tetrafluoroethylenedioxy, cyano and nitro, $R^4$ represents hydrogen or methyl, n is 0, 1 or 2, and $R^2$ and $R^3$ each independently represents methyl, ethyl, n-propyl, isopropyl, n-(iso-, sec-, tert-)butyl, trifluoromethyl, difluoromethyl, 2-methoxyethyl, ethoxymethyl, 2-ethoxyethyl, 2-methylthioethyl, allyl, 2-butenyl, 3-chloroallyl, propargyl, methoxy, ethoxy, n-propoxy, cyclopropyl, cyclopentyl, cyclohexyl, or optionally substituted phenyl or benzyl, having a substituent or substituents selected from the group consisting of fluorine, chlorine, bromine, methyl, ethyl, n-propyl, isopropyl, tert-butyl, trifluoromethyl, methoxy, ethoxy, trifluoromethoxy, methylthio, cyano and nitro, or $R^2$ and $R^3$ together with the adjacent nitrogen atom may form piperidino, morpholino, thiomorpholino, 2,3-dihydroindolyl or perhydroindolyl.

The compounds represented by the general formula (II) and employed as starting materials in the processes according to the present invention can be obtained by the processes disclosed in J. Am. Chem. Soc., vol. 81, pp. 3076–3079 (1959); J. Org. Chem. vol. 45, pp. 5130–5136 (1980) and Japanese Patent Application No. Hei 5-212153.

The compounds represented by the general formula (III) are well known.

The above-mentioned general definitions of radicals or explanations, or those mentioned as preferred, are applicable in a corresponding manner to the end products (I) and to the starting materials (II) and (III) and "intermediates" (IV). These definitions of radicals may be combined with one another, as desired.

Representative 1-substituted-5(4H)-tetrazolinones of the formula (II) include the following compounds:

1-phenyl-5(4H)-tetrazolinone, 1-(3,5-dimethylphenyl)-5(4H)-tetrazolinone, 1-(2-chlorophenyl)-5(4H)-tetrazolinone, 1-(2-chloro-3-methylphenyl)-5(4H)-tetrazolinone, 1-(2-chloro-4-trifluoromethylphenyl)-5(4H)-tetrazolinone, 1-methyl-5(4H)-tetrazolinone, 1-benzyl-5(4H)-tetrazolinone, 1-(3,4-tetrafluoroethylenedioxyphenyl)-5(4H)-tetrazolinone, 1-(2-chloro-5-pyridylmethyl)-5(4H)-tetrazolinone, 1-ethyl-5(4H)-tetrazolinone, 1-n-propyl-5(4H)-tetrazolinone, 1-isopropyl-5(4H)-tetrazolinone, 1-tert-butyl-5(4H)-tetrazolinone, 1-cyclopropyl-5(4H)-tetrazolinone, 1-cyclopentyl-5(4H)-tetrazolinone, 1-cyclohexyl-5(4H)-tetrazolinone, 1-(2,2,2-trifluoroethyl)-5(4H)-tetrazolinone, 1-(2-methoxyethyl)-5(4H)-tetrazolinone, 1-(2-ethylthioethyl)-5(4H)-tetrazolinone, 1-(2-methylthioethyl)-5(4H)-tetrazolinone, 1-allyl-5(4H)-tetrazolinone, 1-(3-chloroallyl)-5(4H)-tetrazolinone, 1-propargyl-5(4H)-tetrazolinone, 1-(2-fluorophenyl)-5(4H)-tetrazolinone, 1-(3-chlorophenyl)-5(4H)-tetrazolinone, 1-(3-trifluoromethylphenyl)-5(4H)-tetrazolinone, 1-(4-trifluoromethylphenyl)-5(4H)-tetrazolinone, 1-(4-chlorophenyl)-5(4H)-tetrazolinone, 1-(2-methylphenyl)-5(4H)-tetrazolinone, 1-(3-methylphenyl)-5(4H)-tetrazolinone, 1-(4-methylphenyl)-5(4H)-tetrazolinone, 1-(2-methoxyphenyl)-5(4H)-tetrazolinone, 1-(4-methoxyphenyl)-5(4H)-tetrazolinone, 1-(4-trifluoromethoxyphenyl)-5(4H)-tetrazolinone, 1-(4-trifluoromethylthiophenyl)-5(4H)-tetrazolinone, 1-(3-propylphenyl)-5(4H)-tetrazolinone, 1-(4-tert-butylphenyl)-5(4H)-tetrazolinone, 1-(2,4-dichlorophenyl)-5(4H)-tetrazolinone, 1-(2,6-dichlorophenyl)-5(4H)-tetrazolinone, 1-(2-chloro-6-methylphenyl)-5(4H)-tetrazolinone,
1-(3-chloro-4-trifluoromethylphenyl)-5(4H)-tetrazolinone,
1-[4-(2,4-dichlorophenoxy)phenyl]-5(4H)-tetrazolinone,
1-[4-(2-chloro-4-trifluoromethylphenoxy)phenyl]-5(4H)-tetrazolinone,
1-[4-(2,6-dichloro-4-trifluoromethylphenoxy)phenyl]-5(4H)-tetrazolinone,
1-(3-phenoxyphenyl)-5(4H)-tetrazolinone,
1-(3,4-difluoromethylenedioxyphenyl)-5(4H)-tetrazolinone,
1-[4-(3,5-dichloropyridin-2-yloxy)-phenyl]-5(4H)-tetrazolinone,
1-[3,5-bis(trifluoromethyl)phenyl]-5(4H)-tetrazolinone,
1-(2-cyanophenyl)-5(4H)-tetrazolinone,
1-(4-chloro-2-fluoro-5-isopropoxyphenyl)-5(4H)-tetrazolinone,
1-[4-chloro-2-fluoro-5-(methoxycarbonyl)methoxyphenyl]-5(4H)-tetrazolinone,
1-[4-chloro-2-fluoro-5-(n-pentyloxycarbonyl)methoxyphenyl]-5(4H)-tetrazolinone,
1-(7-fluoro-4-ethoxy-2H-1,4-benzoxazine-3(4H)-one-6-yl)-5(4H)-tetrazolinone,
1-(7-fluoro-4-propargyl-2H-1,4-benzoxazine-3(4H)-one-6-yl)-5(4H)-tetrazolinone,
1-(6-fluoro-4-propargyl-2H-1,3-benzoxazole-2-one-5-yl)-5(4H)-tetrazolinone,
1-(6-fluoro-4-propargyl-2H-1,3-benzothiazole-2-one-5-yl)-5(4H)-tetrazolinone,
1-[4-chloro-2-fluoro-5-(methanesulfonylamino)phenyl]-5(4H)-tetrazolinone
1-(3-tert-butylisoxazol-5-yl)-5(4H)-tetrazolinone,
1-(5-tert-butylisoxazole-3-yl)-5(4H)-tetrazolinone,
1-(5-tert-butyl-1,3,4-thiazol-2-yl)-5(4H)-tetrazolinone,
1-(5-trifluoromethyl-pyridin-2-yl)-5(4H)-tetrazolinone,
1-(3-chloro-5-trifluoromethyl-pyridin-2-yl)-5(4H)-tetrazolinone,
1-(2-chloroethyl)-5(4H)-tetrazolinone,
1-(2-fluoroethyl)-5(4H)-tetrazolinone, and
1-3(fluoropropyl)-5(4H)-tetrazolinone.

Representative carbamoyl chlorides of the formula (III) include the following compounds:

N,N-dimethyl carbamoylchloride,
N,N-diethyl carbamoylchloride,
N-ethyl-N-methyl carbamoylchloride,
N-ethyl-N-n-propyl carbamoylchloride,
N-ethyl-N-isopropyl carbamoylchloride,
N-ethyl-N-iso-butyl carbamoylchloride,
N-ethyl-N-sec-butyl carbamoylchloride,
N-ethyl-N-tert-butyl carbamoylchloride,
N-ethyl-N-cyclopentyl carbamoylchloride,
N-ethyl-N-cyclohexyl carbamoylchloride,
N,N-di-n-propyl carbamoylchloride,
N-n-propyl-N-isopropyl carbamoylchloride,
N-n-propyl-N-cyclopentyl carbamoylchloride,
N-n-propyl-N-cyclohexyl carbamoylchloride,
N,N-di-isopropyl carbamoylchloride,
N-isopropyl-N-cyclopentyl carbamoylchloride,
N-isopropyl-N-cyclohexyl carbamoylchloride,
N,N-di-n-butyl carbamoylchloride,
N-n-butyl-N-cyclopropyl carbamoylchloride,
N,N-diallyl carbamoylchloride,
N,N-dipropargyl carbamoylchloride,
N-methoxy-N-n-propyl carbamoylchloride,
N-ethoxy-N-n-propyl carbamoylchloride,
N-methyl-N-phenyl carbamoylchloride,
N-ethyl-N-phenyl carbamoylchloride,
N-n-propyl-N-phenyl carbamoylchloride,
N-isopropyl-N-phenyl carbamoylchloride,
N-isopropyl-N-(3-methylphenyl) carbamoylchloride,
N-isopropyl-N-(4-chlorophenyl) carbamoylchloride,
N-isopropyl-N-(4-fluorophenyl) carbamoylchloride,
N-methyl-N-(2-trifluoromethylphenyl) carbamoylchloride,
N-methyl-N-(3-trifluoromethylphenyl) carbamoylchloride,
N-isopropyl-(3-trifluoromethylphenyl) carbamoylchloride,
N-isopropyl-(3-n-propylphenyl) carbamoylchloride,
4-chlorocarbonyl-morpholine,
4-chlorocarbonyl-thiomorpholine,
4-chlorocarbonyl-2,6-dimethylmorpholine,
1-chlorocarbonyl-piperdine,
1-chlorocarbonyl-2,6-dimethylpiperidine,
1-chlorocarbonyl-2,3-dihydroindole, and
1-chlorocarbonyl-perhydroindole.

Process variant (a) according to the invention for the production of the compounds of formula (I) is preferably carried out using diluents. Representative suitable diluents include liquid aliphatic, cycloaliphatic and aromatic, optionally chlorinated, hydrocarbons such as benzene, toluene, xylene, chloroform, chlorobenzene, and the like; ethers such as dioxane, dimethoxyethane (DME), tetrahydrofuran (THF), and the like; ketones such as, for example, acetone, methyl ethyl ketone, methyl isopropyl ketone, methyl isobutyl ketone, and the like; nitrites such as acetonitrile, propionitrile, and the like; esters such as, for example, ethyl acetate, and the like; and liquid bases such as, for example, pyridine, and the like.

Process variant (a) according to the invention is carried out in the presence of 4-dimethylamino-pyridine, which functions not only as acid-binder but also as catalyst.

If 4-dimethylamino-pyridine is employed in only catalytic (sub-stoichiometric) amounts, then process variant (a) is carried out in the presence of an additional acid-binder (in at least stoichiometric amount).

Representative additional acid-binders include inorganic bases such as, for example, carbonates and bicarbonates of alkali metals such as, for example, sodium hydrogen carbonate, potassium hydrogen carbonate, sodium carbonate, potassium carbonate, and the like; and, as organic bases there may be mentioned tertiary amines, dialkylaminoanilines and pyridines such as, for example, triethylamine, 1,1,4,4-tetramethylethylenediamine (TMEDA), N,N-dimethylaniline, N,N-diethylaniline, pyridine, 1,4-diazabicyclo-[2.2.2]octane (DABCO), and 1,8-diazabicyclo-[5,4,0]undec-7-ene (DBU).

In general, the process variant (a) is carried out at a temperature of from about 15° C. to about 150° C., preferably from about 50° C. to about 130° C.

Further, the reaction is preferably carried out under normal pressure, although it is also possible to employ a higher or reduced pressure.

In carrying out process variant (a) according to the invention, the desired compounds of the formula (I) can be obtained in high yields by reacting about 0.8 to 1.5 mols of the compound of the formula (III) per mol of the compound of the formula (II), in the presence of about 0.01 to about 0.5 mols of 4-dimethylamino-pyridine as well as 0.3 to 1.5 mols of an additional acid binder.

In carrying out the process variant (a) with the use of 4-dimethylamino-pyridine as sole acid binder, it may be used in the amount of from about 0.8 to about 1.5 mols, including the desired catalytic amount.

Process variant (b) according to the invention is preferably carried out using diluents. Solvents which are suitable for this purpose are virtually the same organic solvents as have been mentioned above in connection with the description of process variant (a) according to the invention.

The first step of process variant (b) is preferably carried out in the presence of an acid acceptor. Acid-binding agents which are suitable for this purpose are the same as have been mentioned above in connection with the description of process variant (a) according to the invention.

In the second step of process variant (b), there must be employed 4-dimethylamino-pyridine as catalyst for the isomerization reaction (carbamoyl-migration).

In general, the process variant (b) is carried out at a temperature of from about 15° C. to about 150° C., preferably from about 50° C. to about 130° C.

Further, the reaction is preferably carried out under normal pressure, although it is also possible to employ a higher or reduced pressure.

When the above-mentioned process variant (b) according to the present invention is carried out, the compounds of the general formulae (II) and (III), respectively, are reacted in approximately equimolar amounts, followed by reacting the thus prepared mixture of a compound of the general formula (I) and its isomer of the general formula (IV) with about 0.01 to about 0.5 mols of 4-dimethylamino-pyridine as catalyst, so as to obtain the desired tetrazolinones of the general formula (I) in high yields.

The processes according to the present invention are illustrated in the following non-limiting examples hereinbelow in conjunction with the accompanying drawings, wherein FIG. 1 is a graph showing the NMR spectrum of 1-(2-chloro-6-methylphenyl)-5-(N,N-dipropylcarbamoyloxy)-tetrazole of the formula

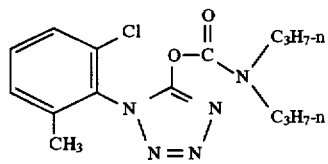

i.e. the "O-carbamoyl" isomer of 1-(2-chloro-6-methylphenyl)-4-(N,N-dipropylcarbamoyl)-5(4H)-tetrazolinone, the latter being described in Synthesis Examples 1–3 and also in Table 1 as Example No. 15.

The "O-carbamoyl" isomer has been synthesized according to Synthesis Example 3, first step, then isolated from the initial mixture of the O-/N-isomers.

EXAMPLES

Synthesis Example 1

[process variant (a)]

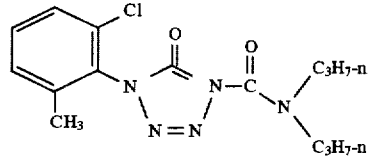

1(2-chloro-6-methylphenyl)-5(4H)-tetrazolinone (0.63 g) and 4-dimethylamino-pyridine (0.44 g) were dissolved in toluene (15 ml) and then dipropylcarbamoyl chloride (0.59 g) was added to the resulting solution, followed by a six-hour refluxing. After the completion of the reaction, the reaction product was purified according to conventional procedure, so as to obtain the desired 1-(2-chloro-6-methylphenyl)-4-(N,N-dipropylcarbamoyl)-5(4H)-tetrazolinone (0.90 g), having a melting point (m.p.) in the range of from 66.5° to 68.5° C. in a yield of 89% of theory.

Figure 3:
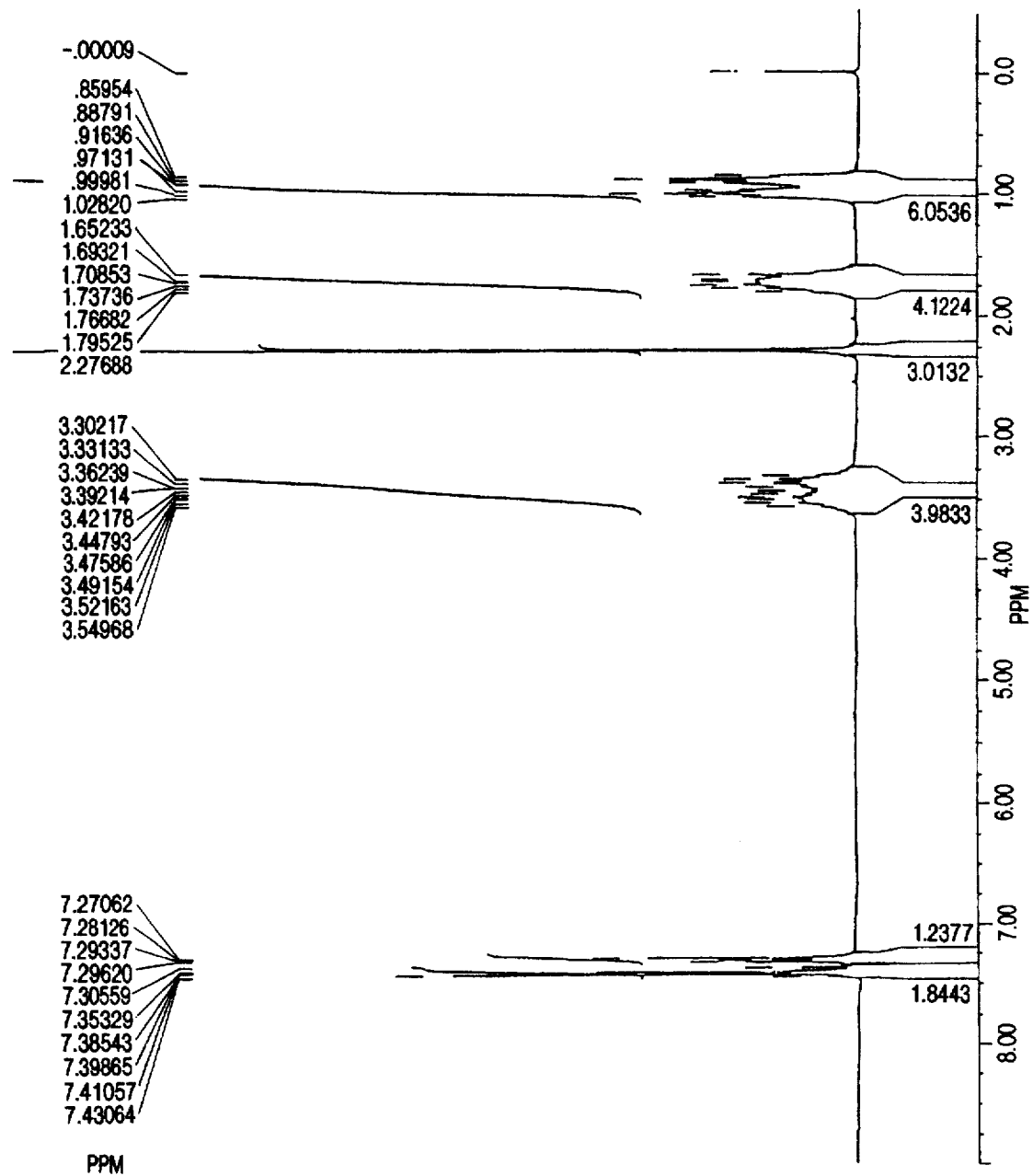
FIG. 3 is a graph showing the NMR spectrum of 1-(2-chloro-6-methylphenyl)-4-(N,N-dipropylcarbamoyl)-5(4H)-tetrazolinone, according to the invention, as described in Synthesis Examples 1–3 and also in Table 1 as Example No. 15.
Figure 4:
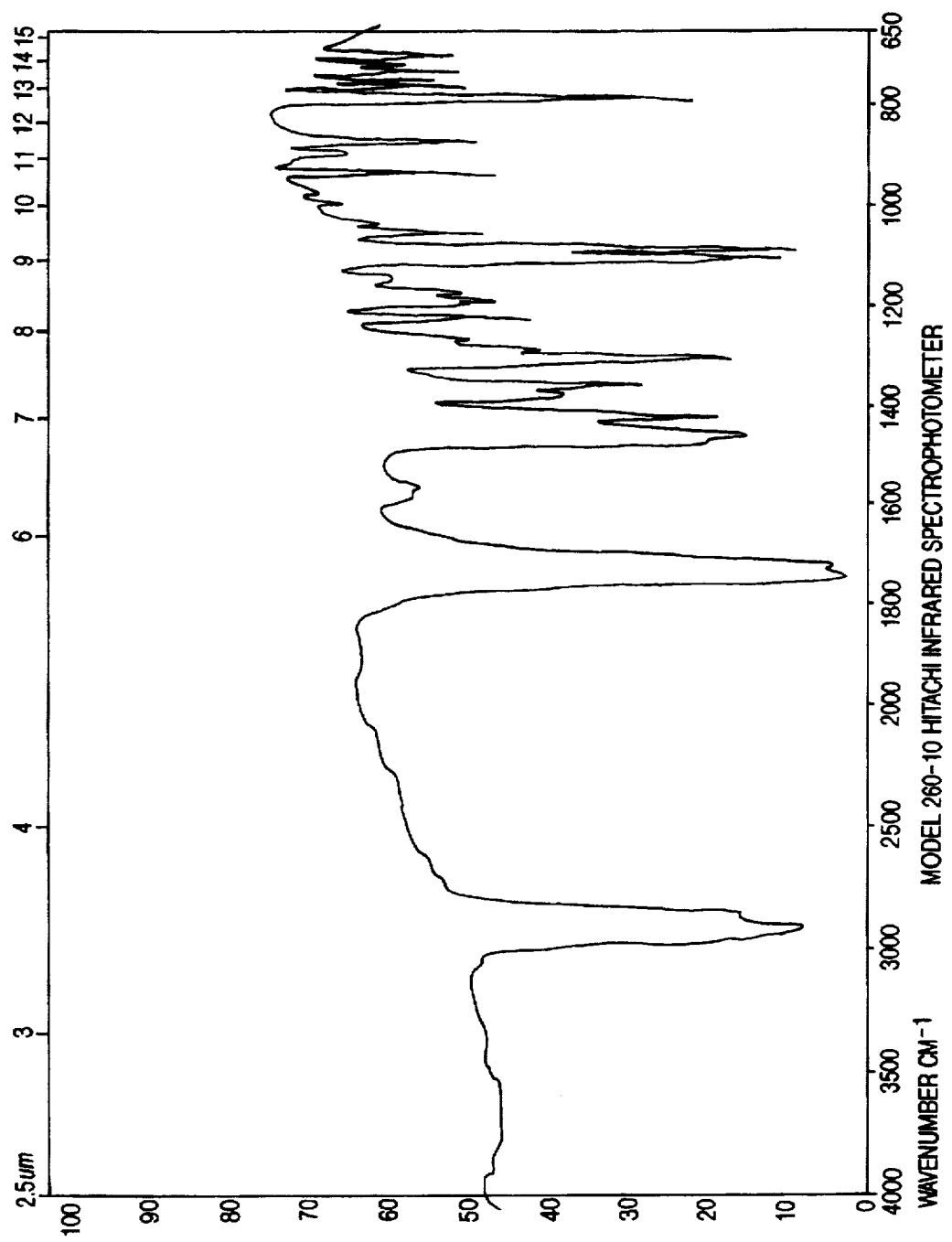
FIG. 4 is a graph showing the IR spectrum of the same compound (in nujol), according to the invention, as in FIG. 3.

N-selectivity: 100% (FIGS. 3 and 4).

Synthesis Example 2

[process variant (a)]

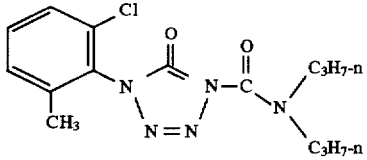

1-(2-chloro-6-methylphenyl)-5(4H)-tetrazolinone (0.63 g), potassium carbonate (0.50 g) and 4-dimethylamino-pyridine (0.037 g) were dissolved in acetonitrile (15 ml) and then dipropylcarbamoyl chloride (0.59 g) was added to the resulting solution, followed by a six-hour refluxing. After the completion of the reaction, the reaction product was purified according to conventional procedure, so as to obtain the desired 1-(2-chloro-6-methylphenyl)-4-(N,N-dipropylcarbamoyl)-5(4H)-tetrazolinone (0.87 g), having a m.p. in the range of from 66.5° to 68.5° C. in a yield of 86% of theory.

N-selectivity: 100% (FIGS. 3 and 4).

Synthesis Example 3
[process variant (b)]

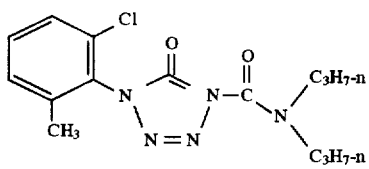

Figure 5:
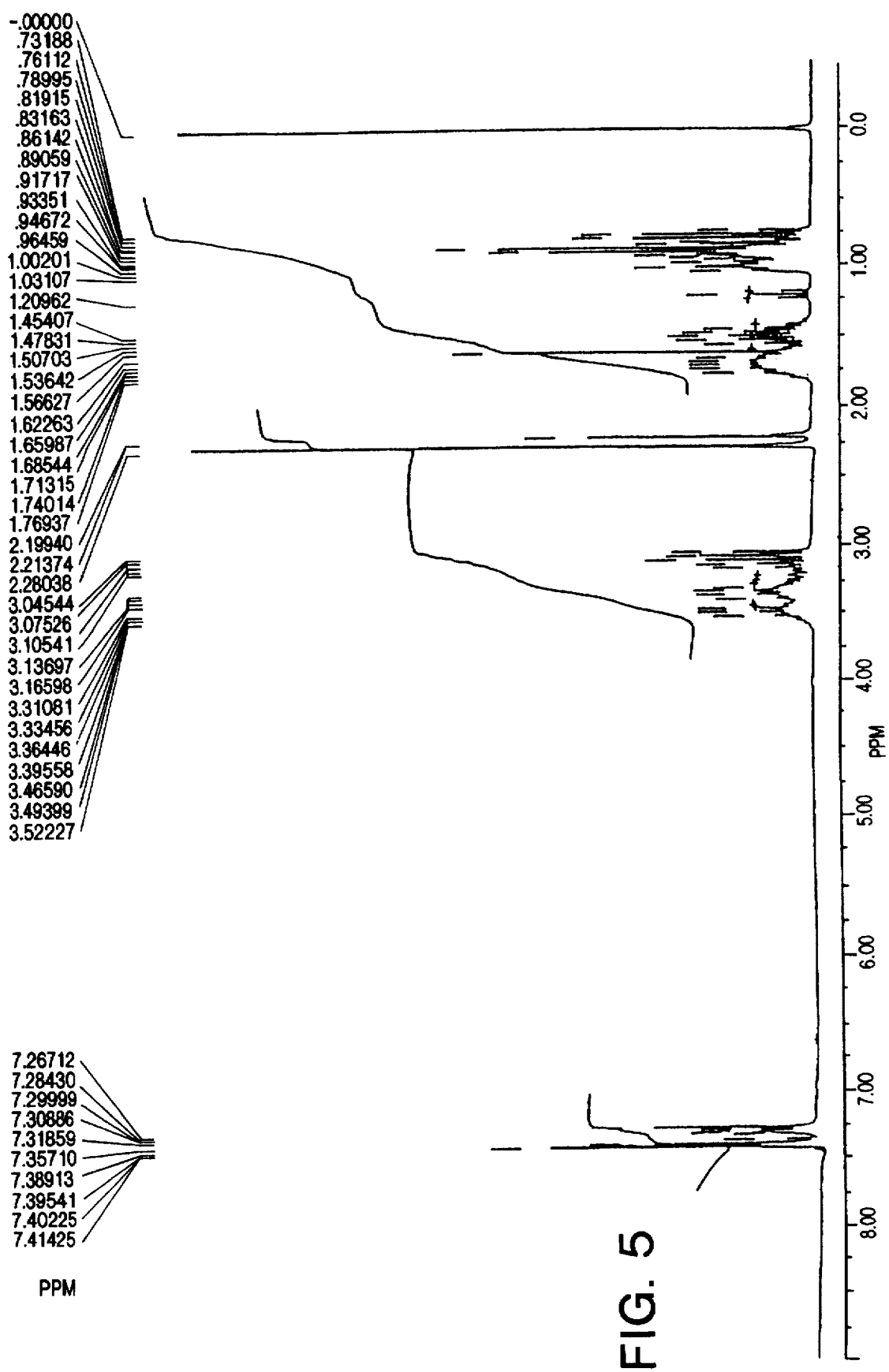
FIG. 5 is a graph showing the NMR spectrum of a (71:29)-mixture of 1-(2-chloro-6-methylphenyl)-4-(N,N-dipropylcarbamoyl)-5(4H)-tetrazolinone and its "O-carbamoyl" isomer, said mixture being obtained according to the first step of Synthesis Example 3.

1-(2-chloro-6-methylphenyl)-5(4H)-tetrazolinone (2.11 g) and potassium carbonate (1.66 g) were mixed in acetonitrile (50 ml) and then dipropylcarbamoyl chloride (1.96 g) was added to the resulting solution, followed by a six-hour refluxing. After the completion of the reaction, the reaction product was purified according to conventional procedure, so as to obtain a mixture (2.93 g) of the desired N-carbamoyl product and the isomeric O-carbamoyl compound (FIG. 5). The N-selectivity of the reaction yielding this mixture turned out to be 71%.

The resulting mixture and 4-dimethylamino-pyridine (0.11 g) were dissolved in acetonitrile (40 ml), followed by a six-hour refluxing. After the completion of the reaction, the reaction product was purified according to conventional procedure, so as to obtain the desired 1-(2-chloro-6-methylphenyl)-4-(N,N-dipropylcarbamoyl)-5(4H)-tetrazolinone (2.51 g), having a m.p. in the range of from 66.5° to 68.5° C. in a yield of 86% of theory.

N-selectivity: 100% (FIGS. 3 and 4).

Figure 1:
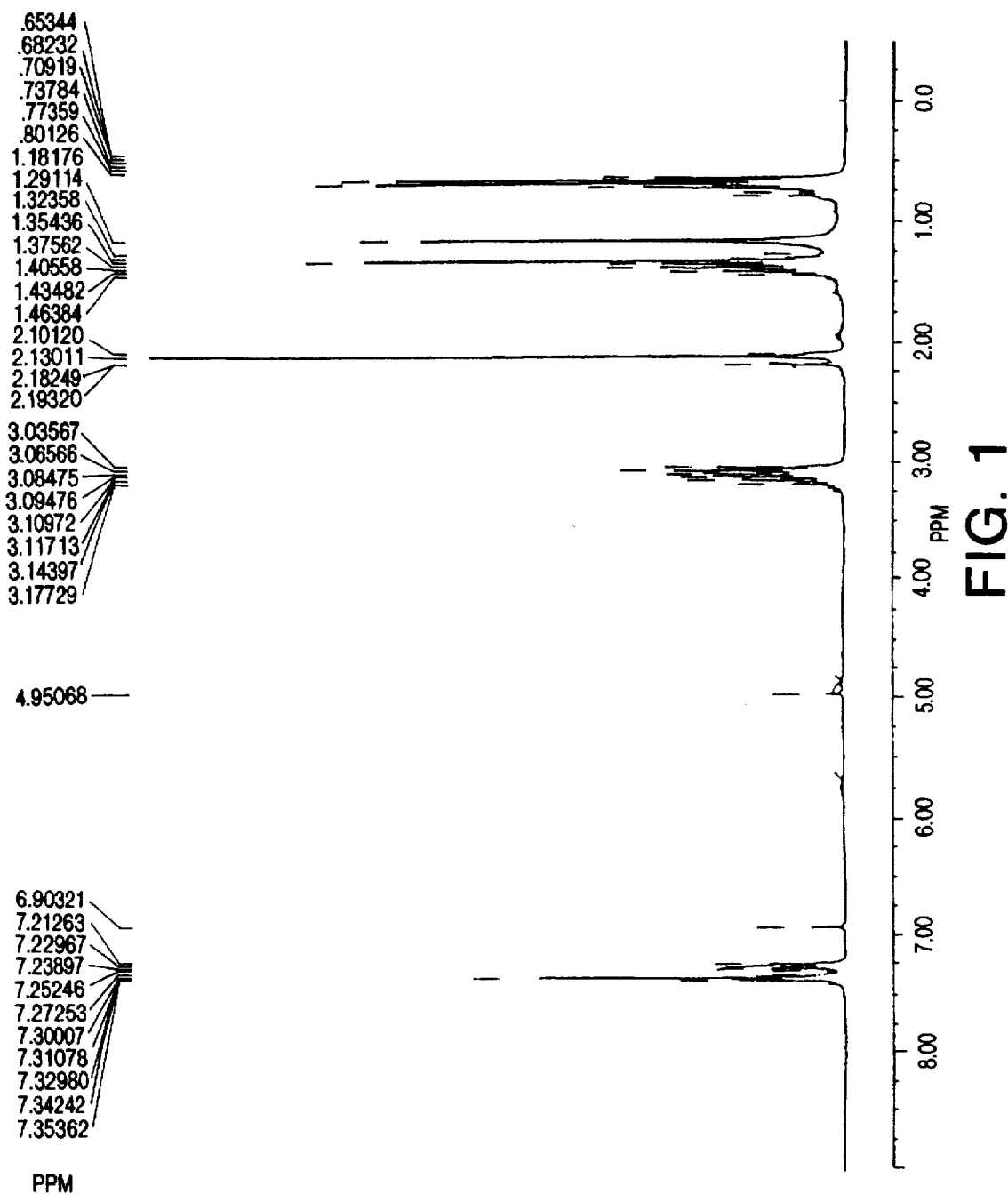
Figure 2:
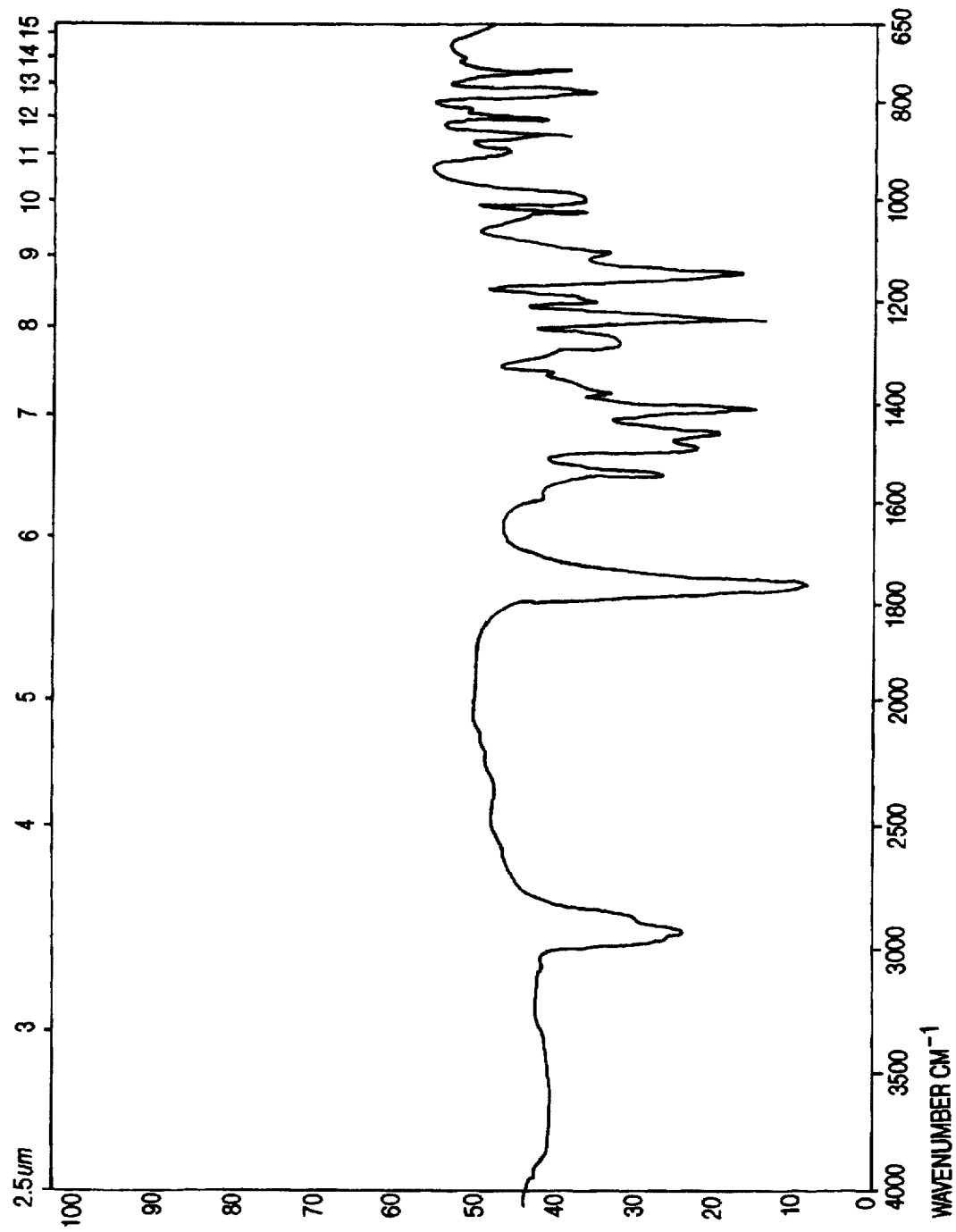
FIG. 2 is a graph showing the IR spectrum of the same "O-carbamoyl" compound (neat) as in FIG. 1.

If desired, the two isomers contained in the above mixture can be separated and isolated in clean form by conventional methods, to determine their individual properties. Thus, the NMR- and IR-spectra of the O-carbamoyl isomer is shown in FIGS. 1 and 2, respectively, while the NMR- and IR-spectra of the N-carbamoyl isomer is shown in FIGS. 3 and 4, respectively.

Further Examples

In analogous manner as described in Synthesis Examples 1–3, there can be obtained the compounds shown in Table 1 which follows; for all listed compounds the N-selectivity proved to be 100% as in the case of the N-carbanoyl compound obtained in said foregoing Synthesis Examples 1–3, such compound being also included in Table 1 as Example No. 15.

TABLE 1

(I)

| Example No. | $R^1$ | $R^2$ | $R^3$ | mp (°C.)/ $n_D^{20}$ |
|---|---|---|---|---|
| 1 | propyl | ethyl | ethyl | 1.4787 |
| 2 | isopropyl | ethyl | ethyl | 1.4763 |
| 3 | t-butyl | ethyl | ethyl | 1.4760 |
| 4 | benzyl | ethyl | ethyl | 1.5321 |
| 5 | phenyl | ethyl | ethyl | 57–61° C. |
| 6 | 2-chlorophenyl | ethyl | ethyl | 1.5415 |
| 7 | 3-chlorophenyl | ethyl | ethyl | 68–75° C. |
| 8 | 4-chlorophenyl | ethyl | ethyl | 89–90.5° C. |
| 9 | 2-methylphenyl | ethyl | ethyl | 68.5–71.5° C. |
| 10 | 2-ethylphenyl | ethyl | ethyl | 1.5263 |
| 11 | 2-isopropylphenyl | ethyl | ethyl | 1.5172 |
| 12 | 2-chloro-6-methyl-phenyl | ethyl | ethyl | 1.5282 |
| 13 | 2-chloro-6-methyl-phenyl | methyl | methyl | 96–98° C. |
| 14 | 2-chloro-6-methyl-phenyl | ethyl | ethyl | 1.5380 |
| 15 | 2-chloro-6-methyl-phenyl | propyl | propyl | 66.5–68.5° C. |
| 16 | 2-chloro-6-methyl-phenyl | propyl | cyclopentyl | 92–93° C. |
| 17 | 2-chlorophenyl | ethyl | propyl | 1.5451 |
| 18 | 2-chlorophenyl | ethyl | butyl | 1.5292 |
| 19 | 2-chlorophenyl | propyl | propyl | 1.5325 |
| 20 | 2-chlorophenyl | propyl | cyclopentyl | 70–73.5° C. |
| 21 | 2-chlorophenyl | ethyl | cyclohexyl | 77.5–79.5° C. |
| 22 | 3-chloro-4-isopropyl-phenyl | ethyl | ethyl | 69.5–72.5° C. |
| 23 | 3-chloro-4-isopropyl-phenyl | allyl | allyl | 47–51° C. |
| 24 | 3-chloro-4-isopropyl-phenyl | propargyl | propargyl | 1.5489 |
| 25 | 3-chloro-4-isopropyl-phenyl | methyl | phenyl | 1.5723 |
| 26 | 3-chloro-4-isopropyl-phenyl | phenyl | phenyl | 113–116.5° C. |
| 27 | 3-chloro-4-isopropyl-phenyl | —(CH$_2$)$_5$— | | 67–70° C. |
| 28 | 3-chloro-4-isopropyl- | —(CH$_2$)$_2$—O—(CH$_2$)$_2$— | | 89.5–92.5° C. |

TABLE 1-continued (I) structure: R¹-N(-N=N-)-C(=O)-N-C(=O)-N(R²)(R³)

| Example No. | R¹ | R² | R³ | mp (°C.)/ $n_D^{20}$ |
|---|---|---|---|---|
|  | phenyl |  |  |  |
| 29 | 3-chloro-4-methyl-phenyl | ethyl | ethyl | 52–57° C. |
| 30 | 3-chloro-4-trifluoro-methoxyphenyl | ethyl | ethyl | 64.5–69.5° C. |
| 31 | 2-chloroethyl | ethyl | ethyl | 1.5013 |
| 32 | 2-chloroethyl | ethyl | isopropyl | 1.5329 |
| 33 | 3-chloropropyl | phenyl | isopropyl | 1.5315 |
| 34 | 2-methoxyethyl | ethyl | ethyl |  |
| 35 | 2-methylthioethyl | ethyl | ethyl |  |
| 36 | cyclopentyl | ethyl | cyclohexyl |  |
| 37 | cyclohexyl | ethyl | cyclohexyl |  |
| 38 | allyl | ethyl | ethyl |  |
| 39 | 3-chloroallyl | ethyl | ethyl |  |
| 40 | propargyl | ethyl | ethyl |  |
| 41 | 1-phenethyl | ethyl | ethyl |  |
| 42 | 2-trifluoromethyl-phenyl | ethyl | ethyl | 90–92° C. |
| 43 | 2-methoxyphenyl | ethyl | ethyl | 76–78° C. |
| 44 | 2-methylthiophenyl | ethyl | ethyl | 82–84° C. |
| 45 | 3-chloro-4-trifluoro-methylthiophenyl | ethyl | ethyl | 61.5–65.5° C. |
| 46 | 2-dimethylamino-phenyl | ethyl | ethyl |  |
| 47 | 2-methoxycarbonyl-phenyl | ethyl | ethyl | 1.5332 |
| 48 | 4-phenoxyphenyl | ethyl | ethyl | 1.5706 |
| 49 | 3,4-methylenedioxy-phenyl | ethyl | ethyl |  |
| 50 | 3,4-ethylenedioxy-phenyl | ethyl | ethyl |  |
| 51 | 2-nitrophenyl | ethyl | isopropyl | 1.5556 |
| 52 | 2-cyanophenyl | ethyl | isopropyl |  |
| 53 | 6-chloro-3-pyridyl-methyl | ethyl | ethyl |  |
| 54 | [substituted benzoxazinone with OC₂H₅ on N] | ethyl | ethyl |  |
| 55 | 3-tert-butyl-5-isoxazolyl | ethyl | ethyl |  |
| 56 | 5-tert-butyl-1,3,4-thiadiazole-2-yl | ethyl | ethyl |  |
| 57 | 5-trifluoromethyl-2-pyridyl | ethyl | ethyl |  |
| 58 | 3-chloro-5-trifluoro-methyl-2-pyridyl | ethyl | ethyl |  |
| 59 | 2-chloro-6-methyl-phenyl | methyl | propyl | 92–94.5° C. |
| 60 | 2-chloro-6-methyl-phenyl | methyl | isopropyl | 120–123 ° C. |
| 61 | 2-chloro-6-methyl-phenyl | ethyl | isopropyl | 1.5288 |
| 62 | 2-chloro-6-methyl-phenyl | ethyl | tert-butyl | 1.5272 |
| 63 | 2-chloro-6-methyl-phenyl | propyl | sec-butyl | 1.5301 |
| 64 | 2-chloro-6-methyl-phenyl | isopropyl | isopropyl | 1.5220 |
| 65 | 2-chloro-6-methyl-phenyl | butyl | butyl | 1.5202 |
| 66 | 2-chloro-6-methyl-phenyl | isobutyl | isobutyl | 86–89° C. |
| 67 | 2-chloro-6-methyl- | methyl | butyl | 1.5322 |

TABLE 1-continued (I)
R¹—N(–N=N–)—C(=O)—N(—C(=O)—NR²R³)

| Example No. | R¹ | R² | R³ | mp (°C.)/ $n_D^{20}$ |
|---|---|---|---|---|
| | phenyl | | | |
| 68 | 2-chlorophenyl | 2-chloro-ethyl | 2-chloro-ethyl | |
| 69 | 2-chlorophenyl | propyl | 2,2,2-tri-fluoroethyl | |
| 70 | 2-chlorophenyl | 2-methoxy-ethyl | 2-methoxy-ethyl | |
| 71 | 2-chlorophenyl | 2-methyl-thioethyl | 2-methyl-thioethyl | |
| 72 | 2-chlorophenyl | 3-chloro-allyl | 3-chloroallyl | |
| 73 | 2-chlorophenyl | ethoxy | ethyl | |
| 74 | 2-chlorophenyl | 3-chloro-allyloxy | ethyl | |
| 75 | 2-chlorophenyl | cyclopropyl | propyl | |
| 76 | 2-chlorophenyl | benzyl | ethyl | |
| 77 | 2-chlorophenyl | 3-chloro-benzyl | ethyl | |
| 78 | 2-chloroethyl | 4-fluoro-phenyl | isopropyl | 1.5221 |
| 79 | 2-chloroethyl | 3-methyl-phenyl | isopropyl | |
| 80 | 2-chloroethyl | 4-trifluoro-methyl-phenyl | isopropyl | |
| 81 | 2-chloroethyl | 2-methoxy-phenyl | isopropyl | |
| 82 | 2-chloroethyl | 4-trifluoro-methoxy-phenyl | isopropyl | |
| 83 | 2-chloroethyl | 4-methyl-thiophenyl | isopropyl | |
| 84 | 2-chloroethyl | 4-trifluoro-methyl-thiophenyl | isopropyl | |
| 85 | 2-chloroethyl | 4-nitro-phenyl | isopropyl | |
| 86 | 2-chloroethyl | 4-cyano-phenyl | isopropyl | |
| 87 | 2-chloroethyl | —(CH₂)₂—S—(CH₂)₂— | | |

It will be understood that the specification and examples are illustrative but not limitative of the present invention and that other embodiments within the spirit and scope of the invention will suggest themselves to those skilled in the art.

We claim:

1. A process for selectivity producing a 1,4-disubstituted-5(4H)-tetrazolinone of the formula

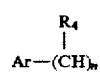

(I)

wherein

R¹ represents $C_{1-2}$ alkyl, $C_{1-6}$ haloalkyl, $C_{2-8}$ alkoxyalkyl, $C_{2-8}$ alkylthioalkyl, $C_{3-8}$ cycloalkyl, $C_{3-8}$ alkenyl, $C_{3-8}$ haloalkenyl, $C_{3-8}$ alkynyl, or

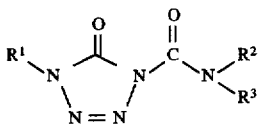

wherein

Ar represents optionally substituted phenyl wherein the substituents are selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxy-carbonyl, carboxyl, phenoxy, heterocyclyl-oxy, methylene dioxy, halomethylene dioxy, ethylene dioxy, haloethylene dioxy, cyano, nitro and —NR⁵R⁶;

and the hetero ring of said heterocycloxy is selected from the group consisting of imidazolyl, pyrazolyl, triazolyl, pyridyl, thienyl, benzothienyl, furan and benzofuran; or Ar represents an optionally substituted naphthyl wherein the substituents are selected from the group consisting of consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxycarbonyl, carboxyl, phenoxy, heterocyclyl-oxy, methylene dioxy, halomethylene dioxy, ethylene dioxy, haloethylene dioxy, cyano, nitro and —NR⁵R⁶;

and the hetero ring of said heterocyclyl-oxy is selected from the group consisting of imidazolyl, pyrazolyl, triazolyl, pyridyl, thienyl, benzothienyl, furan and benzofuran; or Ar represents an optionally substituted five- or six-membered hetero-cyclic ring wherein said hetero ring is selected from the group consisting of imidazolyl, pyrazolyl, triazolyl, pyridyl, thienyl, and furan; wherein the substituents are selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxy-carbonyl, carboxyl, phenoxy, heterocyclyl-oxy, methylene dioxy, halomethylene dioxy, ethylene dioxy, haloethylene dioxy, cyano, nitro and —NR⁵R⁶; and the hetero ring of said heterocyclyl-oxy is selected from the group consisting of imidazolyl, pyrazolyl, triazolyl, pyridyl, thienyl, benzothienyl, furan and benzofuran;

R⁴ represents hydrogen or $C_{1-4}$ alkyl, n represents 0, 1, 2, 3, or 4,

R⁵ and R⁶ are the same or different and represent H or $C_{1-4}$ alkyl,

R² and R³ each independently represent $C_{1-8}$ alkyl, $C_{1-6}$ halogenoalkyl, $C_{2-6}$ alkoxyalkyl, $C_{2-6}$ alkylthioalkyl, $C_{2-6}$ alkenyl, $C_{2-6}$ haloalkenyl, $C_{3-6}$ alkynyl, $C_{1-4}$ alkoxy, $C_{1-4}$ haloalkoxy, $C_{3-8}$ cycloalkyl, optionally substituted phenyl or benzyl wherein the substituents are selected from the group consisting of fluorine, chlorine, bromine, methyl, ethyl, n-propyl, isopropyl, tert-butyl, trifluoromethyl, methoxy, ethoxy, isopropoxy, difluoromethoxy, trifluoromethoxy, methylthio, ethoxy, isopropoxy, difluoromethoxy, trifluoromethoxy, methylthio, ethylthio, trifluoromethylthio, 2,2,2-trifluoroethylthio, cyano and nitro, or R² and R³ together with the adjacent nitrogen atom form piperidino, 2,6-dimethylpiperidino, 2,3-dihydroindolyl or perhydroindolyl, which comprises reacting a compound of the formula

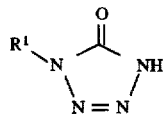 (II)

with a compound of the formula

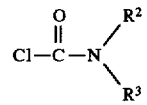 (III)

in the presence of, 4-dimethylaminopyridine which functions as a catalyst and an acid binder, optionally in the presence of a diluent and an additional acid binder at a temperature of 15° C. to 150° C.

2. The process according to claim 1, which contains 0.8 to 1.5 mols of the compound of formula (III) per mol of formula (II), about 0.01 to about 0.5 mols of 4-dimethylaminopyridine and about 0.3 to 1.5 mols of an additional acid binder.

3. The process according to claim 1 wherein the temperature is about 50° C. to about 130° C.

4. A process for selectively producing a 1,4-disubstituted-5(4H)-tetrazolinones of the formula

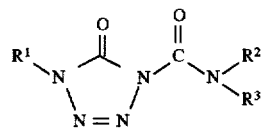 (I)

wherein

R¹ represents $C_{1-12}$ alkyl, $C_{1-6}$ haloalkyl, $C_{2-8}$ alkoxyalkyl, $C_{2-8}$ alkylthioalkyl, $C_{3-8}$ cycloalkyl, $C_{3-8}$ alkenyl, $C_{3-8}$ haloalkenyl, $C_{3-8}$ alkynyl, or

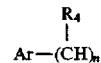

wherein

Ar represents optionally substituted phenyl wherein the substituents are selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxy-carbonyl, carboxyl, phenoxy, heterocyclyl-oxy, methylene dioxy, halomethylene dioxy, ethylene dioxy, haloethylene dioxy, cyano, nitro and —NR⁵R⁶;

and the hetero ring of said heterocycloxy is selected from the group consisting of imidazolyl, pyrazolyl, triazolyl, pyridyl, thienyl, benzothienyl, furan and benzofuran; or Ar represents an optionally substituted naphthyl wherein the substituents are selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxycarbonyl, carboxyl, phenoxy, heterocyclyl-oxy, methylene dioxy, halomethylene dioxy, ethylene dioxy, haloethylene dioxy, cyano, nitro and —NR⁵R⁶;

and the hetero ring of said heterocyclyl-oxy is selected from the group consisting of imidazolyl, pyrazolyl, triazolyl, pyridyl, thienyl, benzothienyl, furan and benzofuran; or Ar represents an optionally substituted five- or six-membered hetero-cyclic ring wherein said hetero ring is selected from the group consisting of imidazolyl pyrazolyl, triazolyl, pyridyl, thienyl, and furan; wherein the substituents are selected from the group consisting of halogen, $C_{1-4}$ alkyl, $C_{1-4}$ haloalkyl, $C_{1-4}$ alkoxy, $C_{1-4}$ haloalkoxy, $C_{1-4}$ alkylthio, $C_{1-4}$ haloalkylthio, $C_{1-4}$ alkoxy-carbonyl, carboxyl, phenoxy, heterocyclyl-oxy, methylene dioxy, halomethylene dioxy, ethylene dioxy, haloethylene dioxy, cyano, nitro and —NR⁵R⁶; and the hetero ring of said heterocyclyl-oxy is selected from the group consisting of imidazolyl, pyrazolyl, triazolyl, pyridyl, thienyl, benzothienyl, furan and benzofuran;

R⁴ represents hydrogen or $C_{1-4}$ alkyl, n represents 0, 1, 2, 3, or 4,

R⁵ and R⁶ are the same or different and represent H or $C_{1-4}$ alkyl,

R² and R³ each independently represent $C_{1-8}$ alkyl, $C_{1-6}$ halogenoalkyl, $C_{2-6}$ alkoxy alkyl, $C_{2-6}$ alkylthioalkyl, $C_{2-6}$ alkenyl, $C_{2-6}$ haloalkenyl, $C_{3-6}$ alkynyl, $C_{1-4}$ alkoxy, $C_{1-4}$ haloalkoxy, $C_{3-8}$ cycloalkyl, optionally substituted phenyl or benzyl wherein the substituents are selected from the group consisting of fluorine, chlorine, bromine, methyl, ethyl, n-propyl, isopropyl, tert-butyl, trifluoromethyl, methoxy, ethoxy, isopropoxy, difluoromethoxy, trifluoromethoxy, methylthio, ethoxy, isopropoxy, difluoromethoxy, trifluoromethoxy, methylthio, ethylthio, trifluoromethylthio, 2,2,2-trifluoroethylthio, cyano and nitro, or $R^2$ and $R^3$ together with the adjacent nitrogen atom form piperidino, 2,6-dimethylpiperidino, 2,3-dihydroindolyl or perhydroindolyl, which comprises (1) reacting a compound of the formula

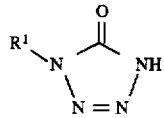

(II)

with a compound of the formula

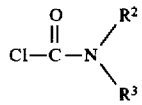

(III)

optionally in the presence of a solvent and of an acid-binder other than 4-dimethylaminopyridine to obtain a mixture of

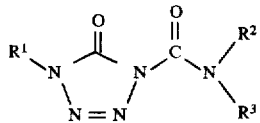

(I)

-continued and

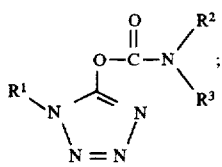

(IV)

and 2) reacting said mixture with 4-dimethylaminopyridine optionally in the presence of a solvent at a temperature from about 15° C. to 150° C.

5. The process according to claim 4, wherein the temperature is about 50° C. to 150° C.

6. The process according to claim 4, which contains approximately equal molar amounts of the compound of formula (I) and formula (II) in the first step and about 0.01 to about 0.5 mols of 4-dimethylaminopyridine in step 2.

* * * * *

UNITED STATES PATENT AND TRADEMARK OFFICE
CERTIFICATE OF CORRECTION

PATENT NO. : 5,767,286
DATED : June 16, 1998
INVENTOR(S) : Yanagi, et al.

It is certified that error appears in the above-identified patent and that said Letters Patent is hereby corrected as shown below:

Col. 15, line 65  Delete " $C_{1-2}$ alkyl " and substitute -- $C_{1-12}$ alkyl --

Col. 16, line 64  Delete " consisting of " (second occurrence)

Col. 18, line 28  Delete " consisting of " (second occurrence)

Signed and Sealed this

Twenty-ninth Day of June, 1999

Attest:

Q. TODD DICKINSON

Attesting Officer

Acting Commissioner of Patents and Trademarks